(12) United States Patent
Vardiman

(10) Patent No.: US 7,729,780 B2
(45) Date of Patent: Jun. 1, 2010

(54) VARIOUS APPARATUS AND METHODS FOR DEEP BRAIN STIMULATING ELECTRODES

(76) Inventor: Arnold B. Vardiman, Whittaker Law Firm, 8 Greenway Plz., Suite 606, Houston, TX (US) 77046

(*) Notice: Subject to any disclaimer, the term of this patent is extended or adjusted under 35 U.S.C. 154(b) by 761 days.

(21) Appl. No.: 11/255,259

(22) Filed: Oct. 21, 2005

(65) Prior Publication Data

US 2006/0122677 A1 Jun. 8, 2006

Related U.S. Application Data

(60) Provisional application No. 60/620,905, filed on Oct. 21, 2004.

(51) Int. Cl.
*A61N 1/05* (2006.01)
(52) U.S. Cl. .......................... 607/116; 607/45
(58) Field of Classification Search ................... 607/116
See application file for complete search history.

(56) References Cited

U.S. PATENT DOCUMENTS

| | | | | |
|---|---|---|---|---|
| 5,788,713 A | * | 8/1998 | Dubach et al. | 606/130 |
| 6,368,330 B1 | * | 4/2002 | Hynes et al. | 606/130 |
| 6,793,670 B2 | * | 9/2004 | Osorio et al. | 607/113 |
| 7,150,737 B2 | * | 12/2006 | Purdy et al. | 604/506 |
| 7,204,833 B1 | * | 4/2007 | Osorio et al. | 606/22 |
| 2003/0187351 A1 | * | 10/2003 | Franck et al. | 600/429 |
| 2004/0082984 A1 | * | 4/2004 | Osorio et al. | 607/105 |
| 2006/0136008 A1 | * | 6/2006 | Tadlock | 607/45 |

* cited by examiner

*Primary Examiner*—Carl H Layno
*Assistant Examiner*—Jeremiah T Kimball
(74) *Attorney, Agent, or Firm*—Whittaker Law Firm; Malcolm E. Whittaker

(57) ABSTRACT

A deploying deep brain stimulating probe with a shaft, at least one opening on said shaft, at least one extendable tendril, said tendril deploying from said shaft into surrounding tissue through said opening and an electrode disposed on said tendril.

15 Claims, 16 Drawing Sheets

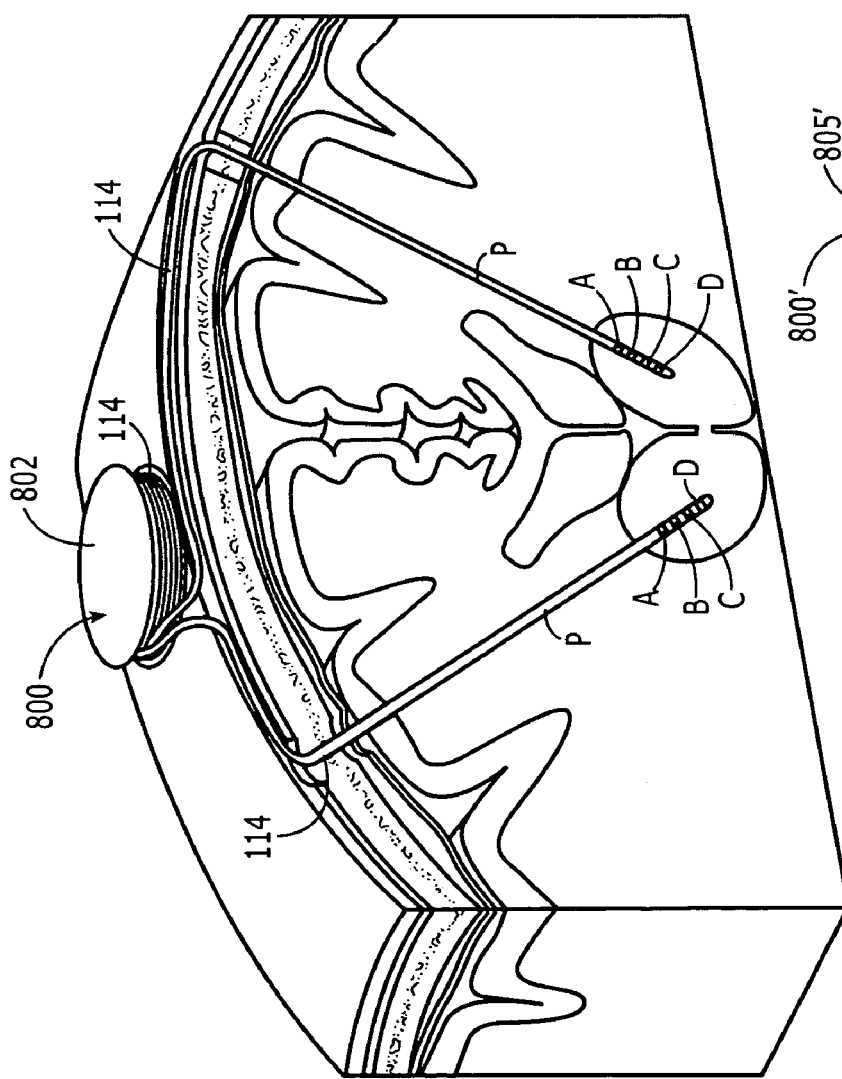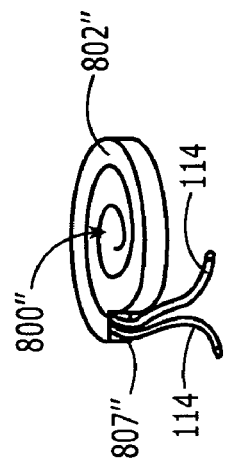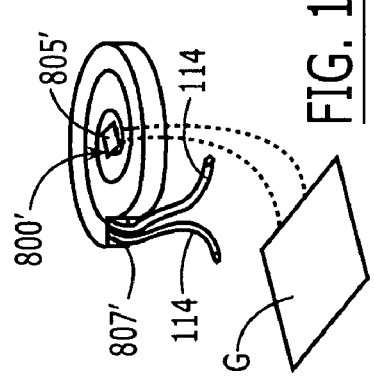

VARIOUS APPARATUS AND METHODS FOR DEEP BRAIN STIMULATING ELECTRODES

RELATED APPLICATION

This application claims priority from U.S. Provisional Patent Application Ser. No. 60/620,905, filed Oct. 21, 2004 and entitled Various Apparatus and Methods for Deep Brain Stimulating Electrodes.

TECHNICAL FIELD OF THE INVENTION

The technical field of the invention relates to deep brain stimulating probes, such as electrodes.

The technical field of the invention relates to delivering infusates, with medicinal properties, into the brain.

The present invention relates to a multi-directional synchronous deploying deep brain stimulating electrodes.

The technical field of the invention relates to a multi-directional selectively deployable deep brain stimulating electrodes.

The present invention relates to a large diameter deep brain stimulating electrodes.

The present invention relates to a curved guide for anatomic arc placement of deep brain stimulating electrode.

The present invention relates to apparatus for delivering infusates, with medicinal properties, into the brain.

The present invention relates to a depth graduated deep brain-stimulating electrode.

The present invention relates to apparatus for labeling, designating target site, uniquely identifying the electrode and/or determining right/left laterality of subcutaneously implanted electrodes, pulse generator connectors (including those with extension kits) or any or all elements of the implanted system.

The present invention relates to subdermal electrode shields.

BACKGROUND OF THE INVENTION

A variety of disabling diseases affecting the central nervous system have proven responsive to treatment using electrical stimulation of specific anatomic targets within the human brain. Examples of disabling diseases affecting the central nervous system are Parkinson's disease, multiple sclerosis and the like.

At the present time, devices designed to produce deep brain stimulation use a standard set of components including a pulse generator and an electrode. The pulse generator is electrically connected to the electrode and the electrode is surgically implanted within a patient's brain. The pulse generator can produce a modulatable electrical field/current. At the present time, the electrode elements have four electrode contacts arranged as narrowly spaced bands on the terminal end of a stimulating electrode.

The physiologic effect of electrical stimulation can be modulated by altering the amplitude, frequency or pulse width of the electrical current, emitted from the electrode deeply implanted within the patient's brain.

Because the current deep brain stimulating probes have four electrodes, it is currently possible to achieve a certain limited degree of flexibility in the electrical "footprint" generated by the electrode by changing which electrode is operating, and the other parameters discussed above.

If the initial surgical placement of the electrode in the brain is sufficiently "off-target," it is impossible to capture the target within the available "footprint" of the electrical field generated by the electrodes of the currently available deep brain stimulating devices.

SUMMARY OF THE INVENTION

The present invention provides for multi-directional synchronous deploying deep brain stimulating electrodes.

The invention provides for multi-directional selectively deployable deep brain stimulating electrodes The present invention provides for large diameter deep brain stimulating electrodes.

The present invention provides for a curved electrode, curved stylet and/or curved guide for anatomic arc placement of a deep brain stimulating electrode.

The present invention provides for apparatus for delivering infusates, with medicinal properties, into the brain.

The present invention provides for depth graduated deep brain-stimulating electrode.

The present invention provides for apparatus for labeling designation target site, uniquely identifying the electrode and/or determining right/left laterality of subcutaneously implanted pulse generator connectors (including those with extension kits) or any other or all elements of the implanted system.

The present invention provides for subdermal electrode shields.

These and other embodiments will be more fully appreciated from the description below.

BRIEF DESCRIPTION OF THE DRAWINGS

FIGS. 1, 1A, 1B, 1C and 1D illustrate use of a current deep brain stimulating probe where the surgeon's initial placement of the probe allows the electrical "footprint" of the electrodes to accurately deliver electrical stimulation to a specific anatomic target within the human brain.

FIG. 1A is a detailed view of the four electrodes seen in FIG. 1.

FIG. 1B is a detailed view of the four electrodes seen in FIG. 1.

FIG. 1C is a detailed view of the four electrodes seen in FIG. 1.

FIG. 1D is a detailed view of the four electrodes seen in FIG. 1.

FIGS. 2, 2A, 2B, 2C and 12D illustrate use of a current deep brain stimulating probe where the surgeon's initial placement of the probe is sufficiently off-target that the electrical "footprint" of the electrodes cannot stimulate the area of the patient's brain requiring electrical stimulation. In other words, the surgeon has missed the target in the patient's brain and must withdraw the probe and reinsert the probe into the patient's brain. This is highly undesirable because it requires the surgeon to make an extra hole in the patient's brain and further traumatizes the patient's brain tissue.

FIG. 2A is a detailed view of the four electrodes seen in FIG. 2 with a first electrode energized.

FIG. 2B is a detailed view of the four electrodes seen in FIG. 2 with a second electrode energized;

FIG. 2C is a detailed view of the four electrodes seen in FIG. 2 with a third electrode energized.

FIG. 12 is a perspective view of a subdermal electrode shield of the present invention implanted beneath a patient's scalp.

FIG. 12A is a perspective view of an alternative embodiment of a subdermal electrode shield.

FIG. 12B is a perspective view of a second alternative embodiment of a subdermal electrode shield.

DESCRIPTION OF THE PREFERRED EMBODIMENTS

Corresponding reference numbers indicate corresponding parts throughout the several views of the drawings and specification.

A variety of disabling diseases affecting the central nervous system have proven responsive to treatment using electrical stimulation of specific anatomic targets T. As such, it is desirable for the electrical field E of stimulating probe P, seen as a shaded area E and also known as an electrical "footprint," to reach the targeted portion T of the human brain, as seen in FIG. 1B.

Figure 1:
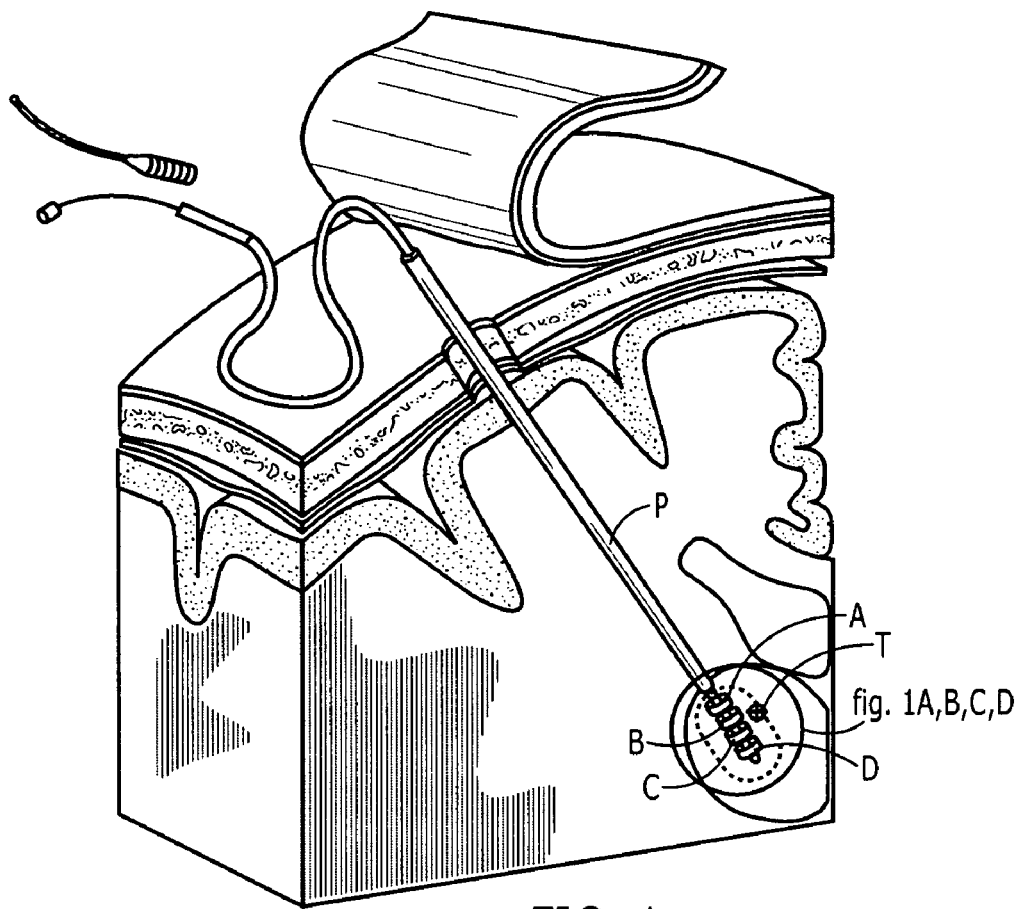
FIG. 1 is perspective view of the current state of the technology, i.e. prior art. The X illustrates the location of the area requiring electrical stimulation in the patient's brain. As noted above, four electrodes are arranged as narrowly spaced bands on the terminal end of the probe.

FIG. 1 illustrates a currently available deep brain stimulation electrode probe P with four electrodes (A, B, C and D) arranged as narrowly spaced bands on the terminal end of a stimulating probe P. The physiologic effect of the stimulation of probe P can be modulated by altering which electrode (A, B, C or D) is energized or by altering the amplitude, frequency or pulse width of the electrical current. However, the four-banded electrodes seen in FIG. 1 are in fixed in position on stimulating probe P. FIG. 1 also shows target T. Target T is depicted by an "X" throughout the present application.

Figure 1A:
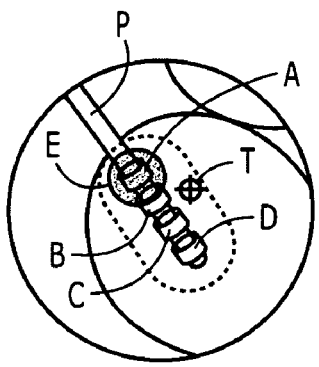

FIG. 1A shows a first electrode A of probe P as it is energized. As can be seen in FIG. 1A, electrical field E does not coincide with Target T and the electrical stimulation provided by electrode A is of limited or no treatment value.

Figure 1B:
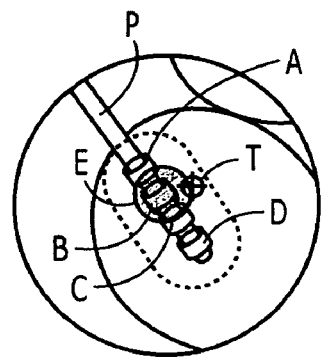

FIG. 1B shows a second electrode B of probe P as it is energized. As can be seen in FIG. 1B, electrical field E coincides with Target T and the electrical stimulation provided by electrode B likely provides therapeutic value to the patient.

Figure 1C:
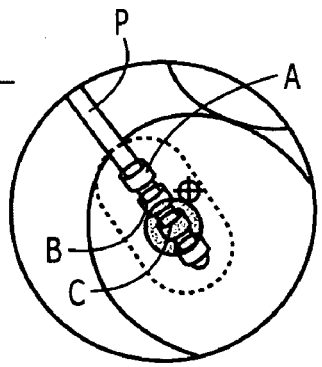

FIG. 1C shows a third electrode C of probe P as it is energized. As can been seen in FIG. 1C, electrical field E does not coincide with Target T and the electrical stimulation provided by electrode C is of limited or no treatment value.

Figure 1D:
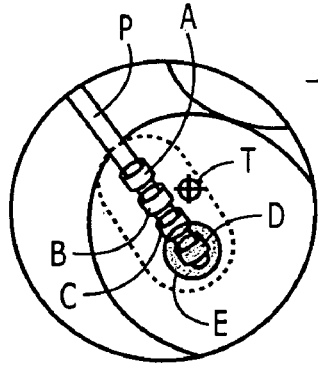

FIG. 1D shows a fourth electrode D of probe P as it is energized. As can been seen in FIG. 1D, electrical field E does not coincide with Target T and the electrical stimulation provided by electrode D is of limited or no treatment value.

Figure 2:
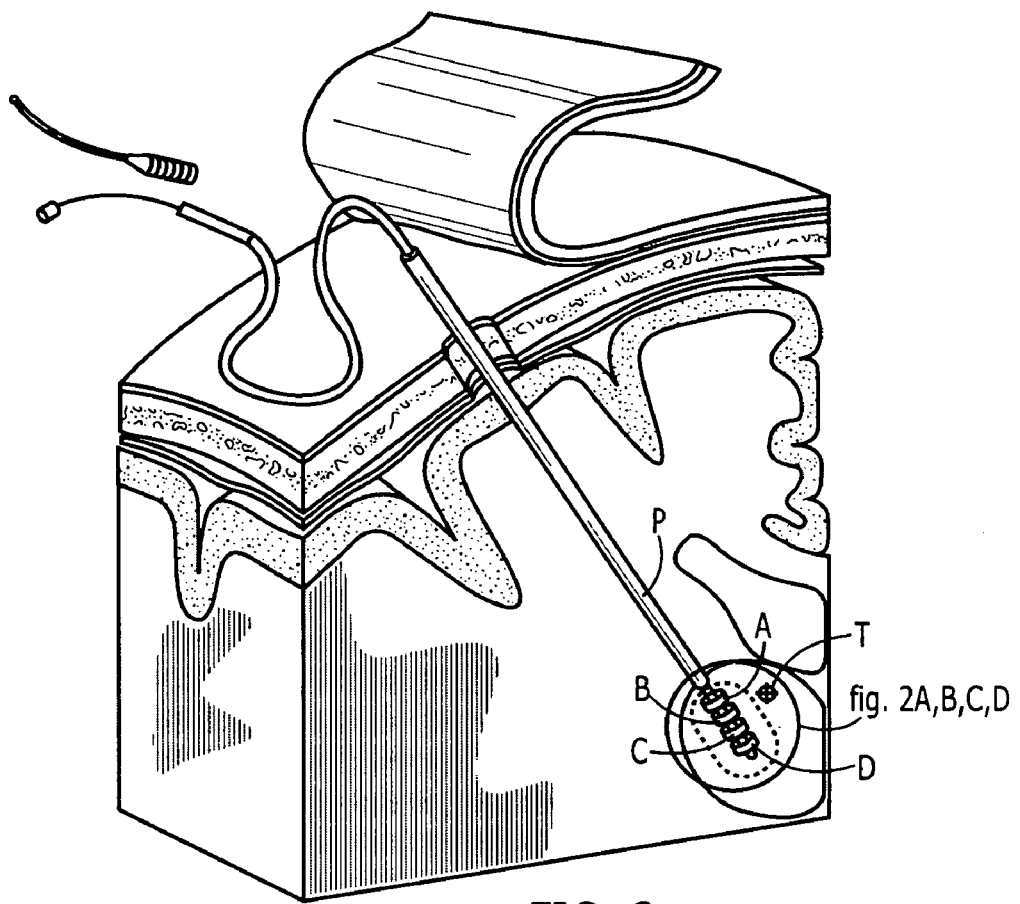
FIG. 2 is perspective view of the current state of the technology, i.e. prior art. The "X" illustrates the location of the area requiring electrical stimulation in the patient's brain. As noted above, four electrodes are arranged as narrowly spaced bands on the terminal end of the probe.

FIG. 2 illustrates a potential situation where a surgeon's initial surgical placement of probe P is sufficiently off target such that it may be impossible to capture target T with the available electrical field E. In this situation, the surgeon may have to withdraw probe P and reinsert it into the patient's brain. This is considered undesirable because the surgeon will have to make a second hole through the patient's brain.

Figure 2A:
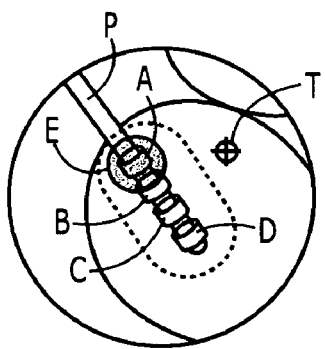

FIG. 2A shows a first electrode A of probe P as it is energized. As can be seen in FIG. 2A, electrical field E does not coincide with Target T and the electrical stimulation provided by electrode A is of limited or no treatment value.

Figure 2B:
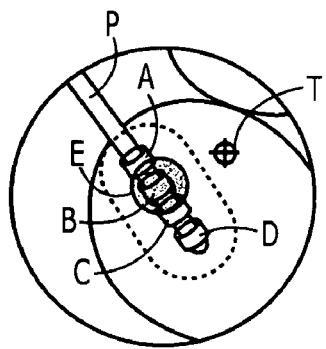

Unlike FIG. 1B, FIG. 2B shows a second electrode B of probe P as it is energized. As can be seen in FIG. 2B, electrical field E does not coincide with Target T and the electrical stimulation provided by electrode B is of limited or no treatment value.

Figure 2C:
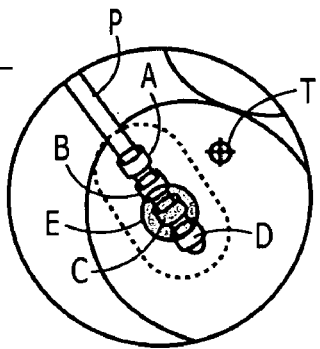

FIG. 2C shows a third electrode C of probe P as it is energized. As can been seen in FIG. 2C, electrical field E does not coincide with Target T and the electrical stimulation provided by electrode C is of limited or no treatment value.

Figure 2D:
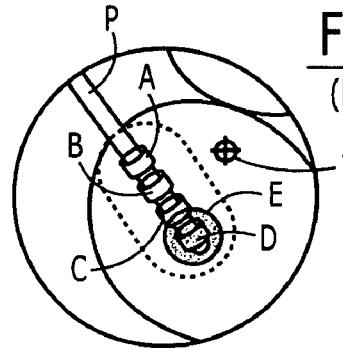
FIG. 2D is a detailed view of the four electrodes seen in FIG. 2 with a fourth electrode energized.

FIG. 2D shows a fourth electrode D of probe P as it is energized. As can been seen in FIG. 2D, electrical field E does not coincide with Target T and the electrical stimulation provided by electrode D is of limited or no treatment value.

Figure 3:
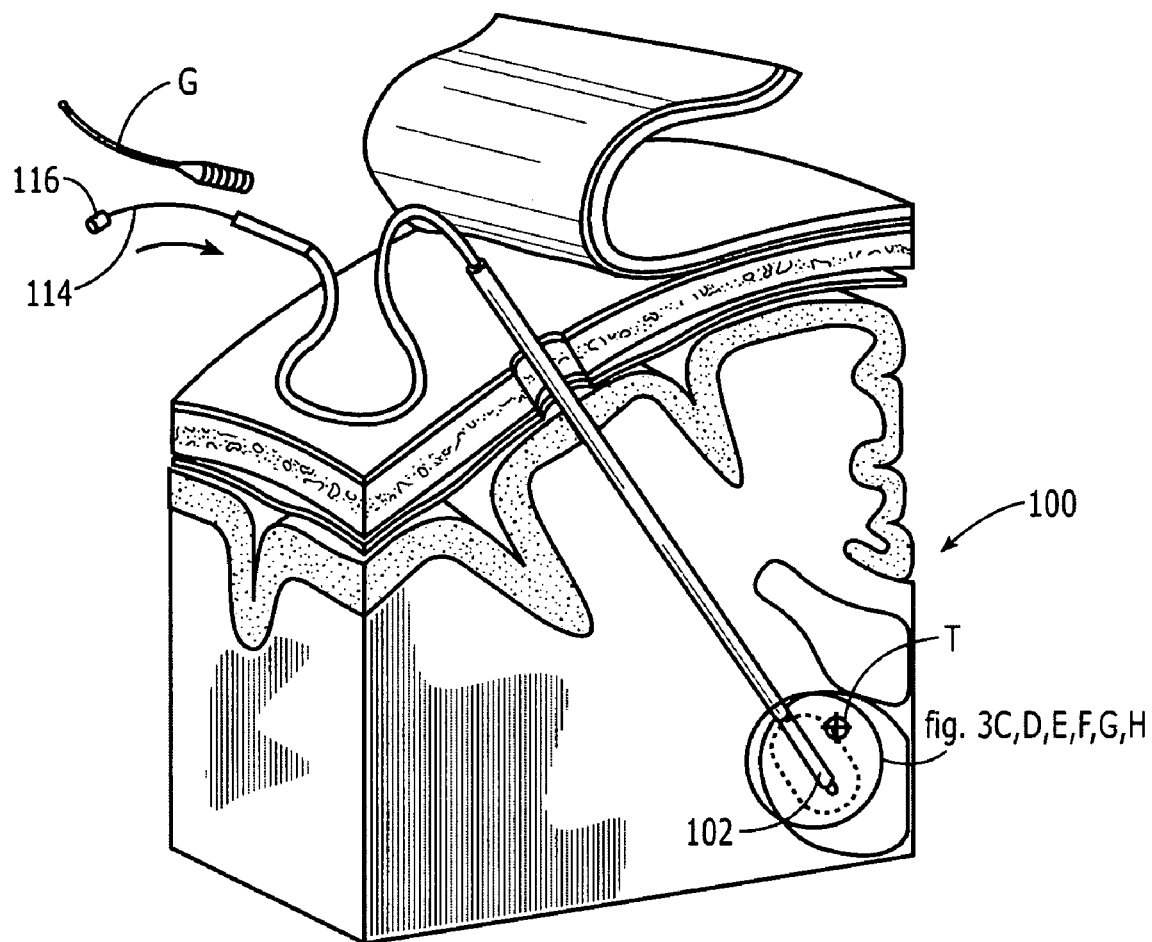
FIG. 3 is a perspective view of the multi-directional synchronous deploying deep brain stimulating electrodes of the present invention.

FIG. 3 shows a perspective view of a multi-directional synchronous deploying deep brain stimulation probe 100 implanted within a human brain. Probe 100 includes shaft 102, sleeve 104, openings 106, stiffener 108 and tendrils 110. Probe 100 is placed using standard techniques such as frame based, frameless or image guided placement techniques. FIGS. 3 shows probe 100 positioned within the human brain.

Figure 3A:
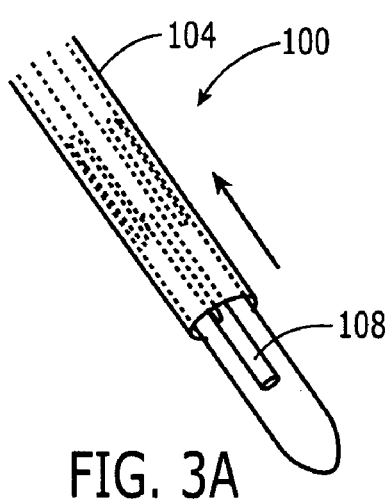
FIG. 3A is a detailed perspective view of the present invention seen in FIG. 3 with the electrodes undeployed.
Figure 3B:
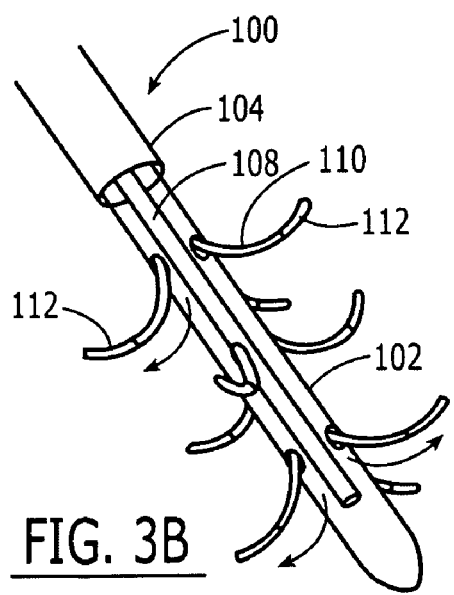
FIG. 3B is a detailed perspective view of the present invention seen in FIGS. 3 and 3A with the electrodes deployed.

FIGS. 3A and 3B show stiffener 108. A surgeon may elect to use stiffener 108 if he desires a more rigid probe 100. A surgeon electing to use a less rigid probe 100, would use elect to remove stiffener 108.

FIG. 3A shows sleeve 104 repositioned such that multiple tendrils 110 advance in a gentle trajectory into the surrounding brain tissue through openings 106, as seen in FIG. 3B. FIG. 3B also shows electrodes 112.

FIG. 3 shows line 114 and connector 116. Line 114 interconnects electrodes 112 to pulse generator G. Pulse generators G are well known in the prior art.

Figure 3C:
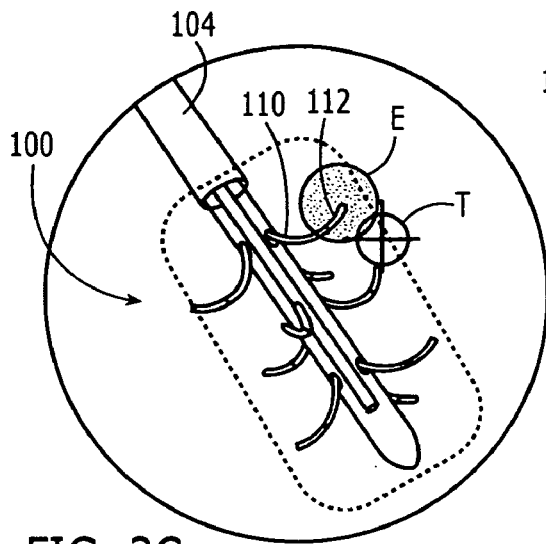
FIG. 3C is a detailed perspective view of the present invention seen in FIGS. 3 and 3A with a first electrode energized.

FIGS. 3 and 3C-3H show probe 100 in use. Specifically, FIG. 3C shows probe 100 with a first tendril 110 extended and electrode 112 energized. The electrical field E generated by electrode 112 is shown as the shaded area throughout the figures in the present patent application. As seen in FIG. 3C, electrical field E does not coincide with target T. As such, the electrical stimulation provided by electrode 112 is of limited or no treatment value.

Figure 3D:
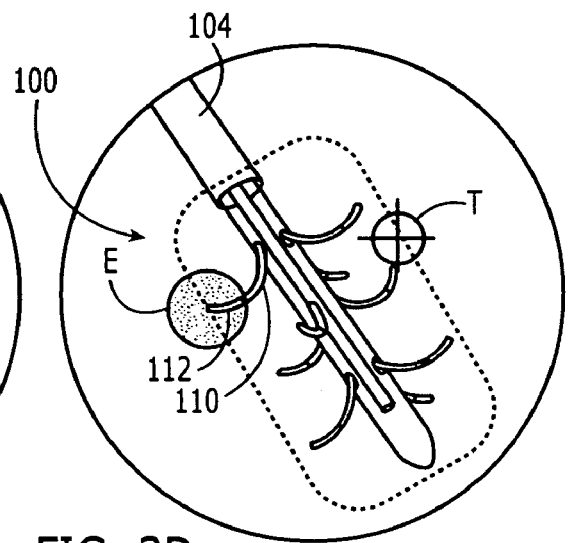
FIG. 3D is a detailed perspective view of the present invention seen in FIGS. 3 and 3A with a second electrode energized.

FIG. 3D shows a probe 100 with a second tendril 110 extended and electrode 112 energized. Because the electrical field E does not coincide with target T, the electrical stimulation provided by electrode 112 is of limited or no treatment value.

Figure 3E:
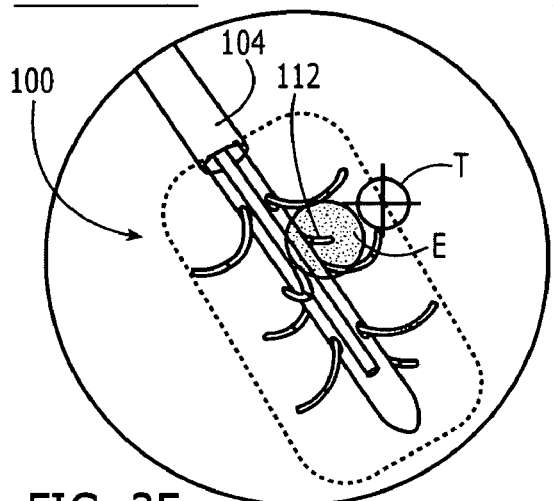
FIG. 3E is a detailed perspective view of the present invention seen in FIGS. 3 and 3A with a third electrode energized.

FIG. 3E shows a probe 100 with a third tendril 110 extended and electrode 112 energized. Because the electrical field E does not coincide with target T, the electrical stimulation provided by electrode 112 is of limited or no treatment value.

Figure 3F:
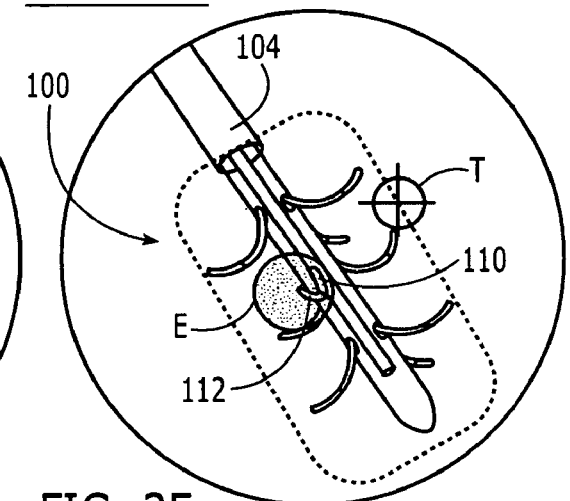
FIG. 3F is a detailed perspective view of the present invention seen in FIGS. 3 and 3A with a fourth electrode energized.

FIG. 3F shows a probe 100 with a fourth tendril 110 extended and electrode 112 energized. Because the electrical field E does not coincide with target T, the electrical stimulation provided by electrode 112 is of limited or no treatment value.

Figure 3G:
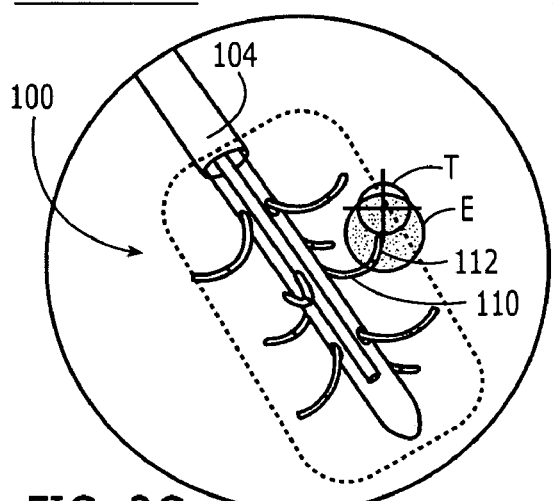
FIG. 3G is a detailed perspective view of the present invention seen in FIGS. 3 and 3A with a fifth electrode energized.

FIG. 3G shows a probe 100 with a fifth tendril 110 extended and electrode 112 energized. Because the electrical field E coincides with target T, the electrical stimulation provided by electrode 112 likely provides therapeutic value to the patient.

Figure 3H:
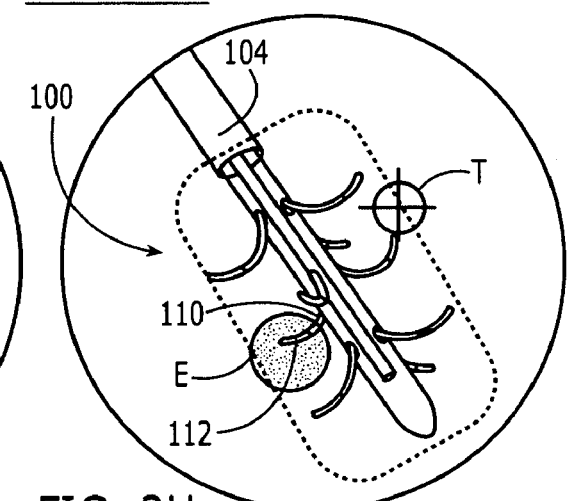
FIG. 3H is a detailed perspective view of the present invention seen in FIGS. 3 and 3A with a sixth electrode energized.

FIG. 3H shows a probe 100 with a sixth tendril 110 extended and electrode 112 energized. Because the electrical field E does not coincide with target T, the electrical stimulation provided by electrode 112 is of limited or no treatment value.

It is also within the scope of the present invention to include a brainwave reader 118 [seen in FIG. 3H]. Preferably, brain wave reader 118 would be sufficiently small that it could fit on tendrils 110 of probe 100. It is also within the scope of the present invention that multiple probes 100 could be implanted within a patient's brain with each tendril 110 including a brain wave reader 118 or brain wave readers 118 on only selected tendrils 110. Use of a brain wave reader 118 could allow a closed-loop system where selected electrodes 112 are energized in response to undesirable patterns of neural activity.

If one or more probes 100, or any other type of probe shown or described in the present application or its equivalent, were implanted within a patient's brain, an external brain wave reader [not shown] could use the information generated by the brain wave monitors 118 to record neural activity and to "map" neural activity. In other words, probe 100 could monitor neural activity and also deliver electrical stimulation in response to detected patterns of neural activity in a patient. For example, the early stages of an epileptic seizure generate a recognizable pattern of neural activity in the human brain. One or more brain wave monitors 118 could detect the pattern of neural activity and energize one or more electrodes 112 on one or more probes 100 in order to counteract the undesirable neural activity patterns. It is within the scope of the present invention that undesirable neural activity such as found with seizures, depression or tremors or the like, could be counteracted by using brain wave monitors 118 to detect the undesirable patterns and energizing the appropriate sequence of electrodes 112 to reduce or eliminate such undesirable neural activity patterns. As discussed later in this application, infusates might also be delivered into the patient's brain to counter-act undesirable patterns of brain wave activity. This infusion of infusates could be in conjunction with energizing the appropriate sequence of electrodes 112 to reduce or eliminate such undesirable neural activity patterns.

Similarly, a partially or fully paralyzed person, because of a damaged or severed spinal column, might have one or more probes 100 implanted in their brain. As discussed above, each probe 100 would include an electrode 112 and a brain wave monitor 118. The brain wave monitors 118 would "map" the paralyzed person's brain wave patterns when the patient was thinking about performing a particular body function. For example, if a paralyzed person were instructed to think about moving their left foot forward, the brain wave monitors 118 would record this pattern of neural activity. Obviously, the patient's left foot would not move because the patient is paralyzed and there is either a damaged or severed electrical connection between the patient's brain and the nerves and muscles of the patient's left foot. However, the pattern of neural activity associated with moving the patient's left foot forward would be stored within an external brain wave reader [not shown]. It is well known which groups of muscles move a human's left foot forward. Once the neural pattern for moving the left foot is recorded by the external brain wave reader [not shown], each time this pattern of neural activity is detected in the patient's brain, electrodes implanted in the patient's body could be energized to stimulate the patient's muscles to move the patient's left foot forward. In this way, the external brain wave reader [not shown] would "learn" to mimic the range of motion for a paralyzed patient and thereby replace the severed or damaged spinal cord. Obviously, the present invention is not limited to forward motion of the left foot. In fact, it is considered that it is within the scope of the present invention that a patient could relearn how to control the areas of his body that are not in communication with his or her brain because of a severed or damaged spinal cord.

It is contemplated that any type of deep brain stimulation probe that is disclosed by this application could accomplish the goal of restoring motion to a paralyzed person and this disclosure is not limited to a multi-directional synchronous deploying deep brain stimulation probe 100.

Figure 4:
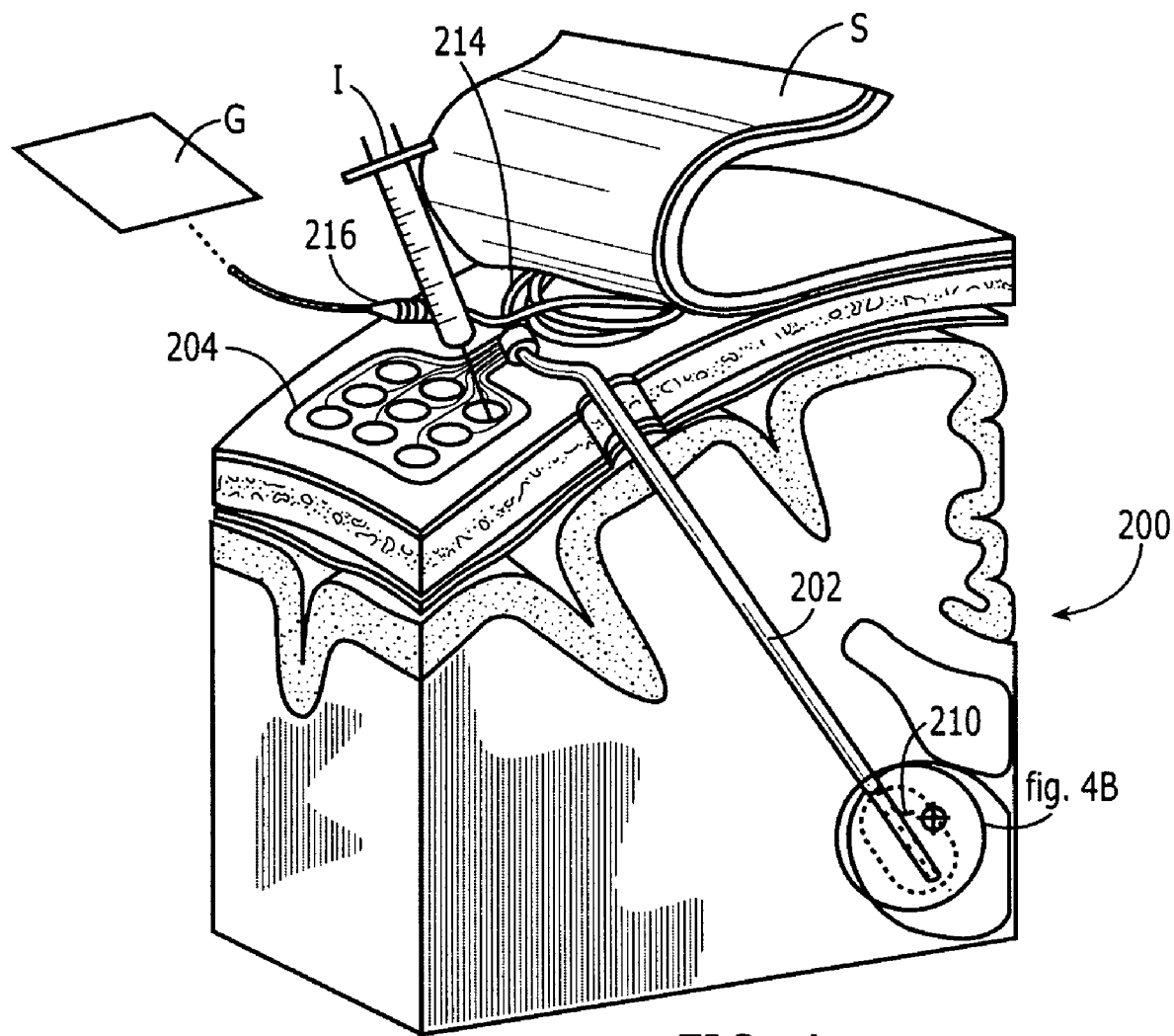
FIG. 4 is a perspective view of the multi-directional selectively deployable deep brain stimulation electrodes of the present invention with the patient's scalp opened to expose the underlying tissue.

FIG. 4 shows multi-directional selectively deployable deep brain stimulation probe 200 implanted within a human brain. Probe 200 includes shaft 202, reservoir 204, openings 206, stiffener 208 and tendrils 210. Probe 200 is placed using standard techniques such as frame based, frameless or image guided placement techniques.

Figure 4A:
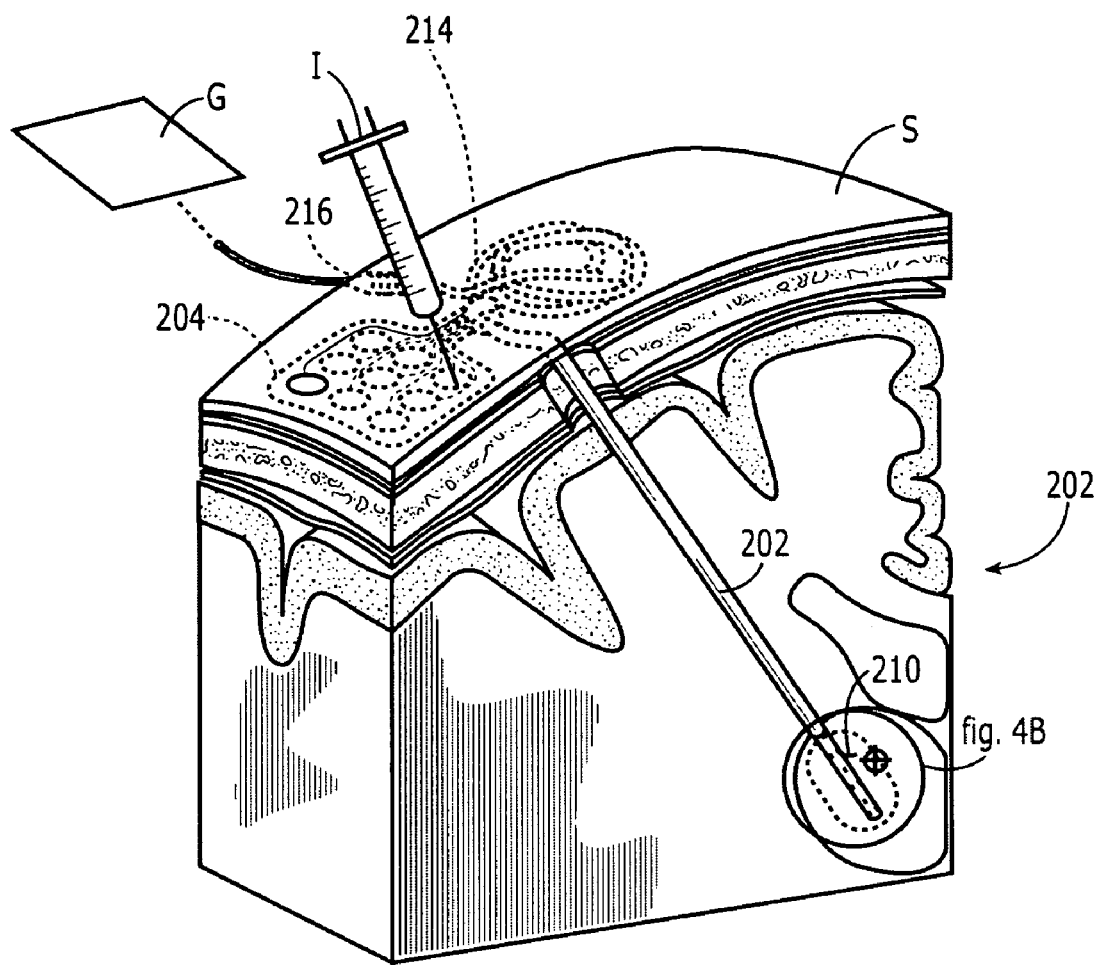
FIG. 4A is a perspective view of the multi-directional selectively deployable deep brain stimulating electrodes of the present invention in use with the patient's scalp replaced. This embodiment allows use of the device outside of an operating room environment.
Figure 4B:
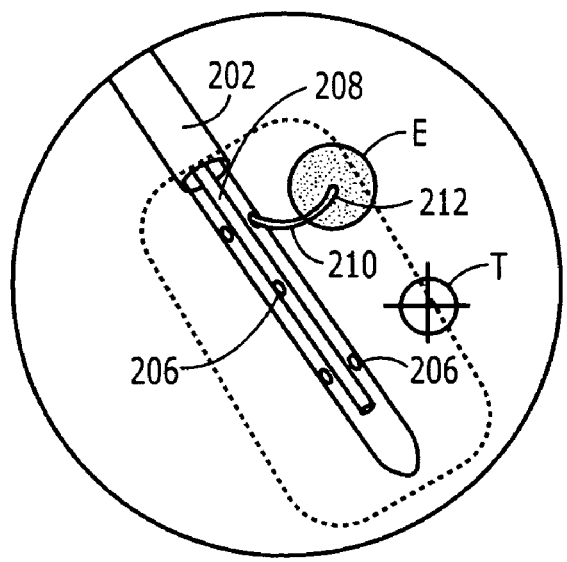
FIG. 4B is a detailed perspective view of the present invention of the present invention seen in FIGS. 4A and 4B with a first electrode deployed and energized.

FIG. 4 shows probe 200 positioned within the human brain. FIGS. 4A and 4BB show a stiffener 208. A surgeon may elect to use stiffener 208 if he desires a more rigid probe 200. A surgeon electing to use a less rigid probe 200, would use elect to remove stiffener 208.

FIGS. 4, 4A and 4B show reservoirs 204 in communication with tendrils 210. It is within the scope of the invention that reservoirs 204 could selectively urge tendrils 210 advance in a gentle trajectory into the surrounding brain tissue through openings 206, as seen in FIG. 4B. Specifically, reservoirs 204 could be hydraulic reservoirs, mechanical or electrical devices, or other similar mechanism that would urge one or more tendrils 210 to advance out of openings 206. Hydraulic reservoirs 204 are shown by way of example. However, other means of urging tendrils 210 outward are within the scope of the present invention. FIG. 4B also shows electrodes 212. Electrodes 212 are preferably at the ends of tendrils 210.

FIG. 4 shows line 214 and connector 216. Line 214 interconnects electrodes 212 to pulse generator G. Pulse generators G are well known in the prior art.

FIGS. 4 and 4B shows a syringe injecting hydraulic fluid into one of the cavities of reservoir 204. When hydraulic fluid is urged into the cavity seen in FIG. 4, tendril 210, seen in FIG. 4B, is urged out from opening 206 and tendril 210 advances in a gentle trajectory into the surrounding brain tissue. After tendril 210 extends into the surrounding brain tissue, electrode 212 is energized and creates electrical field E. In the example shown in FIG. 4B, target T and electrical field E do not coincide and the electrical stimulation provided by electrode 212 is of limited or no treatment value.

FIG. 4A shows multi-directional selectively deployable deep brain stimulation probe 200 with scalp S replaced. Using probe 200 with scalp S replaced is vitally important for operation of probe 200 outside of an operating room environment. Because probe 200 can operate with scalp S replaced, injector I must pass through scalp S in order to access reservoirs 204. As discussed above, when tendril 210 extended outward and electrode 212 energized, either with scalp S pulled back (FIG. 4) or replaced (FIG. 4A), electrical field E did not coincide with target T and the electrical stimulation provided by electrode 212 is of limited or no treatment value. As such, a surgeon will select an alternative cavity of reservoir 204 in order to urge a second tendril 210 outward.

Figure 5:
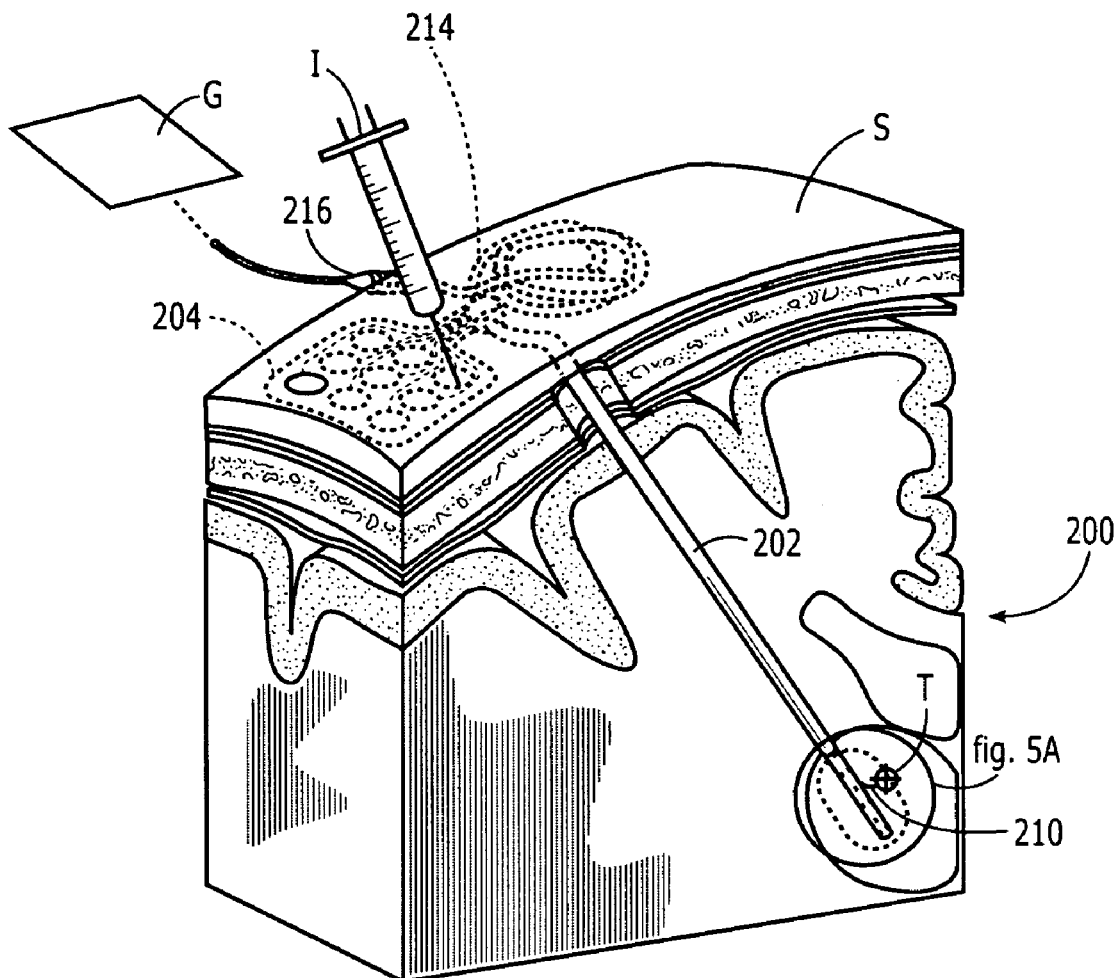
FIG. 5 is a perspective view of the multi-directional selective deployable deep brain stimulation electrodes of the present invention with an electrode energized.
Figure 5A:
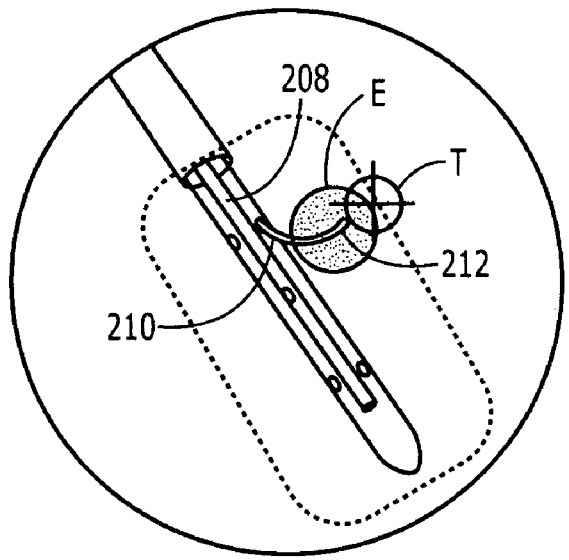
FIG. 5A is a detailed perspective view of the energized electrode seen in FIG. 5.

FIGS. 5 and 5A show a surgeon selecting an alternative cavity of reservoir 204 in order to urge a second tendril 210 outward. As seen in FIG. 5A, the surgeon has chosen the correct cavity of reservoir 204 and tendril 210 is urged outward through openings 206. When electrode 212 is energized, electrical field E coincides with target T and the electrical stimulation provided by electrode 112 likely provides therapeutic value to the patient.

Figure 6:
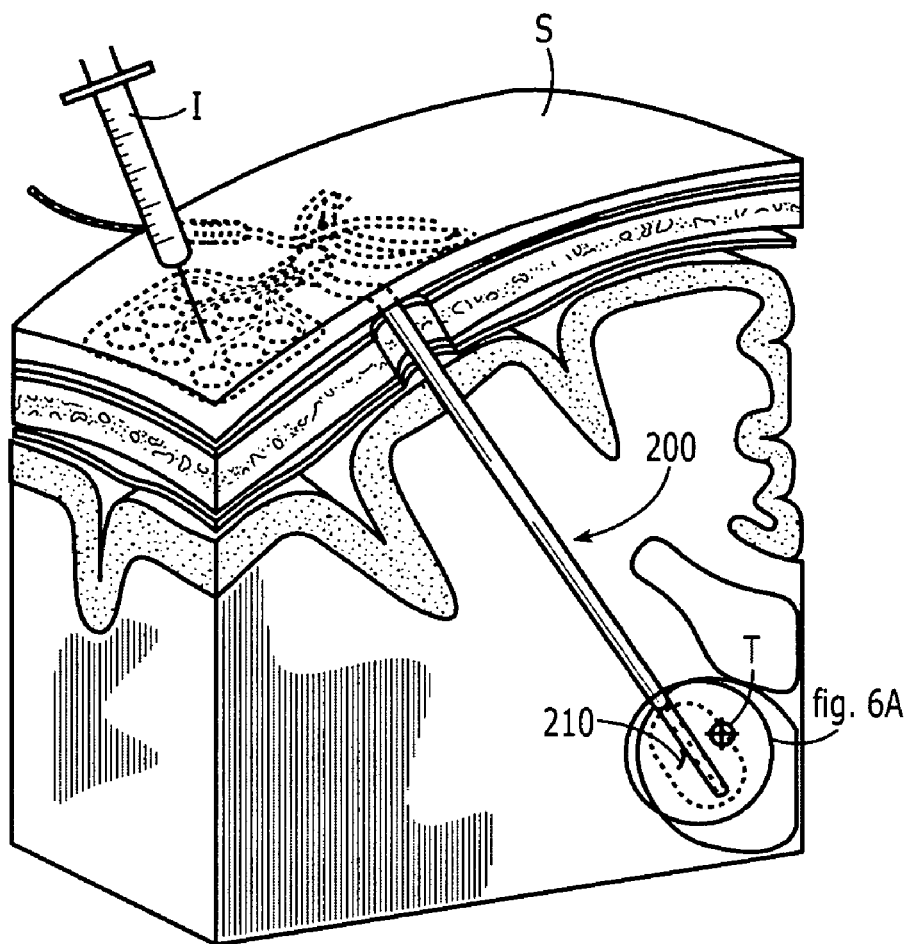
FIG. 6 is a perspective view of the multi-directional selective deployable deep brain stimulation electrodes of the present invention with an electrode energized.
Figure 6A:
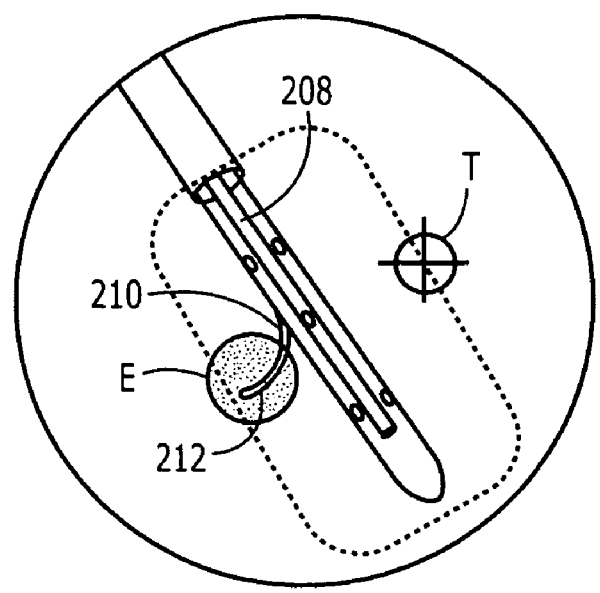
FIG. 6A is a detailed perspective view of the deployed and energized electrode seen in FIG. 6.

FIGS. 6 and 6A show a surgeon selecting a third cavity in reservoir 204 and illustrates how tendril 210 is selectively urged outward through opening 206. Because target T has already been electrically stimulated, FIGS. 6 and 6A are included to emphasize that tendrils 210 of probe 200 are selectively deployable.

Figure 7:
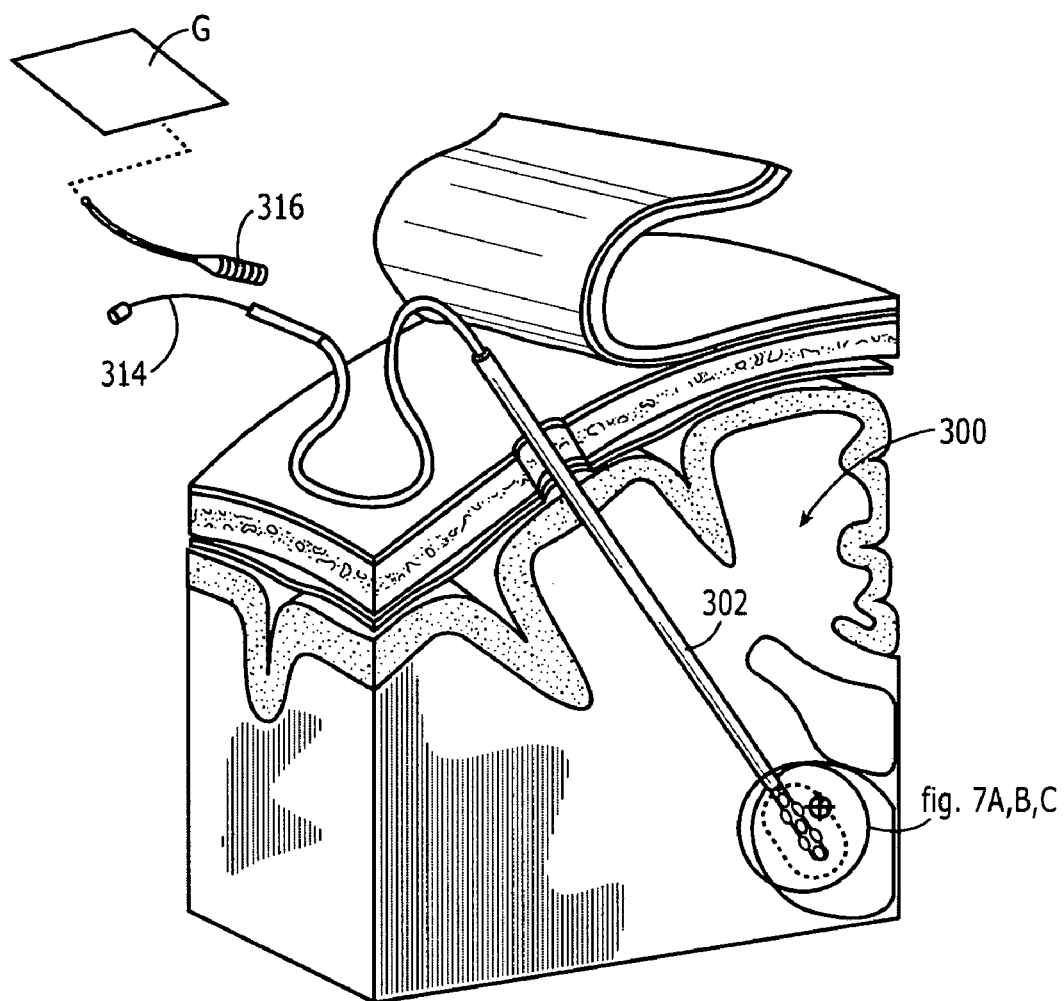
FIG. 7 is a perspective view of the large diameter deep brain stimulation electrode of the present invention.
Figure 7A:
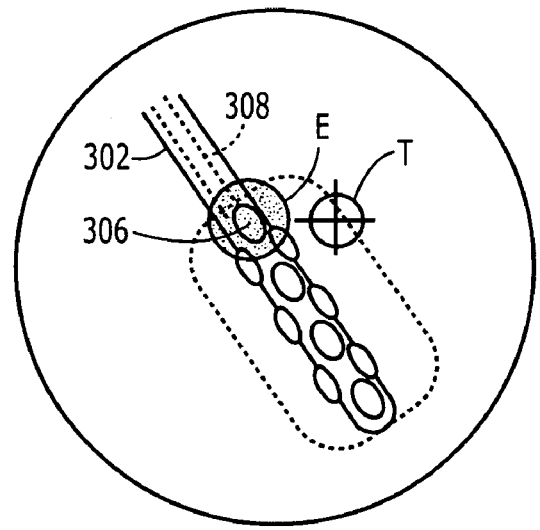
FIG. 7A is a detailed perspective view of the large diameter deep brain stimulation electrode of the present invention with a first electrode energized.
Figure 7B:
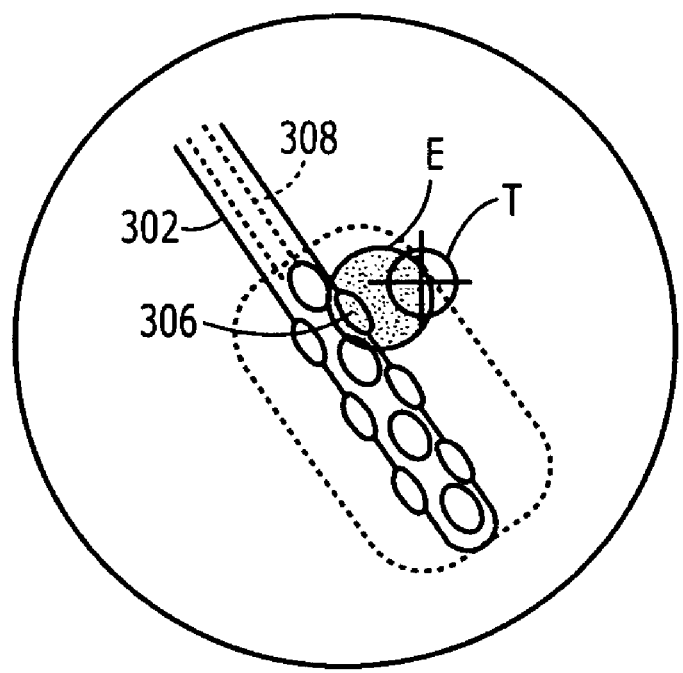
FIG. 7B is a detailed perspective view of the large diameter deep brain stimulation electrode of the present invention with a second electrode energized.

FIGS. 7, 7A and 7B show a perspective view of a large diameter deep brain stimulation probe 300 implanted within a human brain. Probe 300 includes shaft 302, placodes 306 and stiffener 308. Probe 300 is placed using standard techniques such as frame based, frameless or image guided placement techniques.

FIG. 7 shows probe 300 positioned within the human brain. FIG. 7A shows stiffener 308. A surgeon may elect to use stiffener 308 if he desires a more rigid probe 300. A surgeon electing to use a less rigid probe 300, would use elect to remove stiffener 308.

FIG. 7A shows placode 306 positioned on probe 300. In one embodiment, small multiple placodes 306 are radially oriented and staggered along the length of shaft 302. When each placode 306 is energized, placode 306 generates an electrical field E, such as seen in FIG. 7A. As seen in FIG. 7A, when first placode 306 is energized, electrical field E did not coincide with target T and the electrical stimulation provided by placode 306 is of limited or no treatment value. As such, a surgeon will select an alternative placode 306 to energize.

FIG. 7B shows when a second placode 306 is energized by a surgeon. Second placode 306 creates and electrical field E. When second placode 306 is energized, electrical field E coincides with target T and the electrical stimulation provided by placode 306 likely provides therapeutic value to the patient.

Figure 7C:
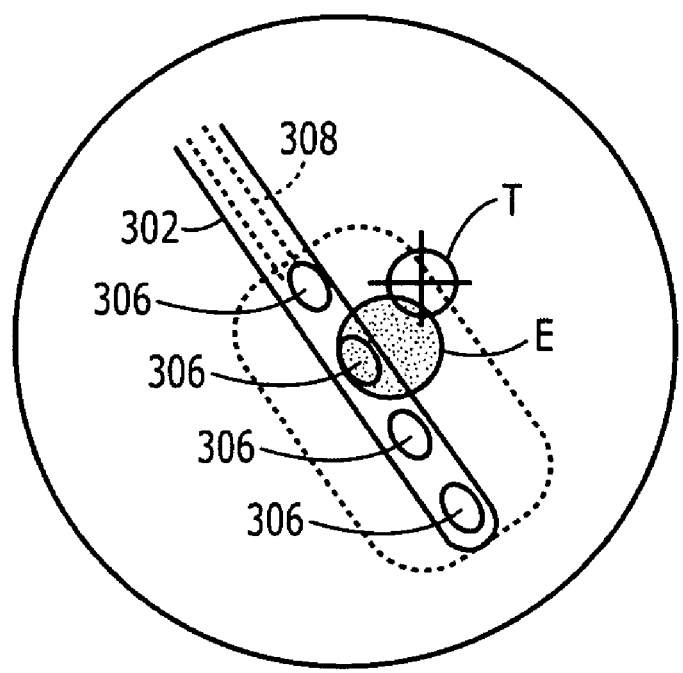
FIG. 7C is a detailed perspective view of an alternative embodiment of the large diameter deep brain stimulation electrode of the present invention.

FIG. 7C shows an alternative embodiment of probe 300. In the alternative embodiment of probe 300 seen in FIG. 7C, placodes 306 are placed "single-file" along the longitudinal axis of probe 300 so that a simple rotation of probe 300 will allow modulation of the direction of electrical field E.

FIG. 7 also shows line 314 and connector 316. Line 314 interconnects placodes 306 to pulse generator G. Pulse generators G are well known in the prior art.

Figure 8A:
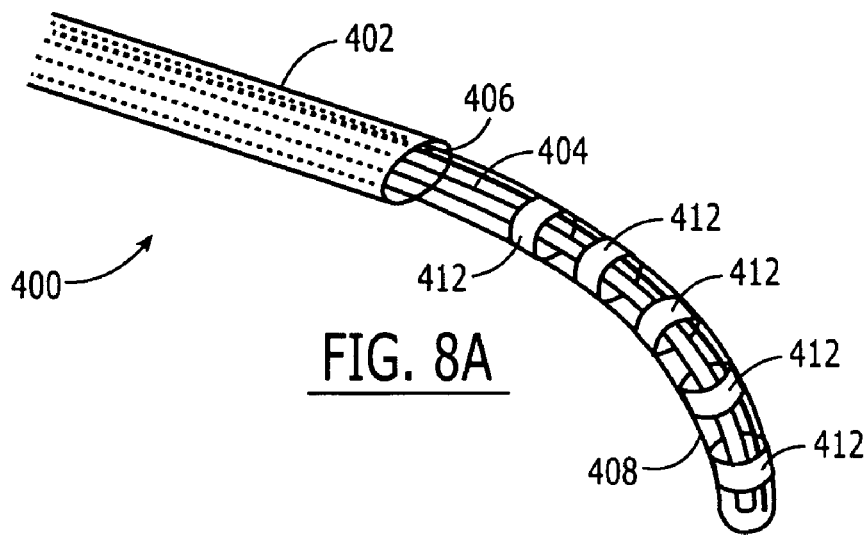
FIG. 8A is a perspective view of the curved guide for anatomic arc placement of a deep brain stimulation electrode of the present invention.

FIG. 8A is a perspective view of the curved guide for anatomic arc placement of a deep brain stimulation electrode 400 of the present invention. Probe 400 includes catheter 402, groove 404, orientation guide rail 406, electrodes 412, line 414 and connector 416. Probe 400 is desirable because it is undesirable for a probe to pass through certain structures in the human brain. As such, probe 400 can be pre-curved to a shape to avoid certain neural structures in the human brain. Groove 404 and orientation guide rail 406 cooperatively guide shaft 408. As seen in FIG. 8C, electrodes 412 are disposed at regular intervals along shaft 408.

Figure 8B:
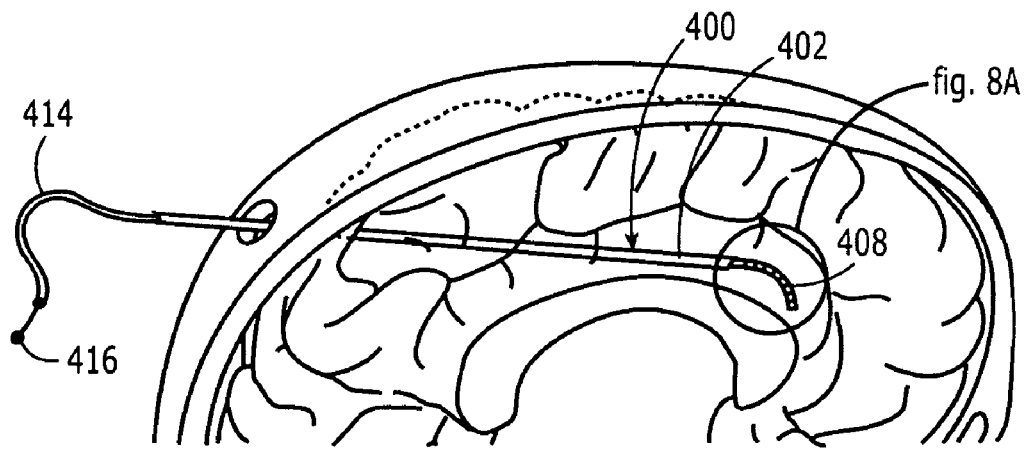
FIG. 8B is curved guide for anatomic arc placement of a deep brain stimulation electrode shaped so as to avoid the cingulate gyrus of the human brain.
Figure 8C:
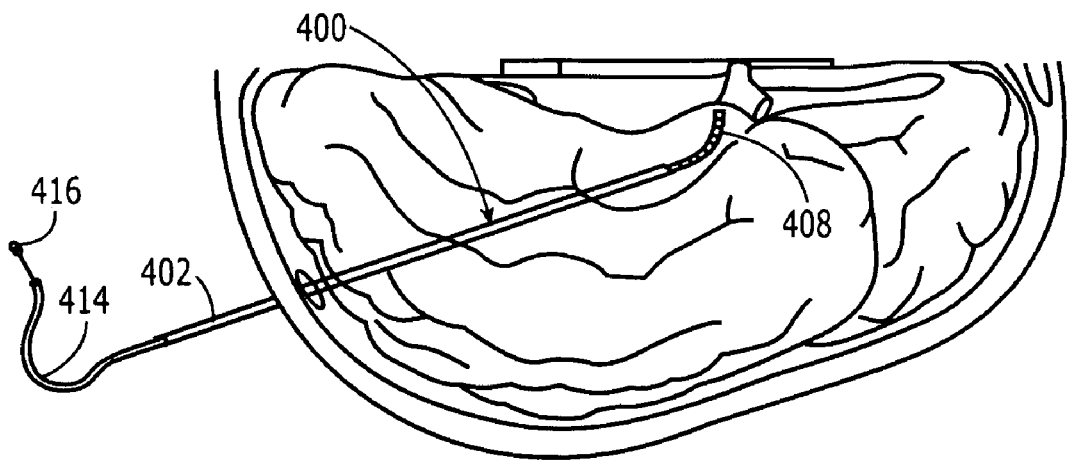
FIG. 8C is a curved guide for anatomic arc placement of a deep brain stimulation electrode shaped so as to avoid the mesial temporal lobe structures of the human brain.

FIG. 8B shows probe 400 curved guide for anatomic arc placement of a deep brain stimulation electrode shaped so as to avoid the cingulate gyrus of the human brain.

FIG. 8C is a curved guide for anatomic arc placement of a deep brain stimulation electrode 400 shaped so as to avoid the mesial temporal lobe structures of the human brain. It is within the scope of the present invention that probe 400 could be pre-curved to more readily allow a surgeon to avoid structures within in the human brain.

Figure 9:
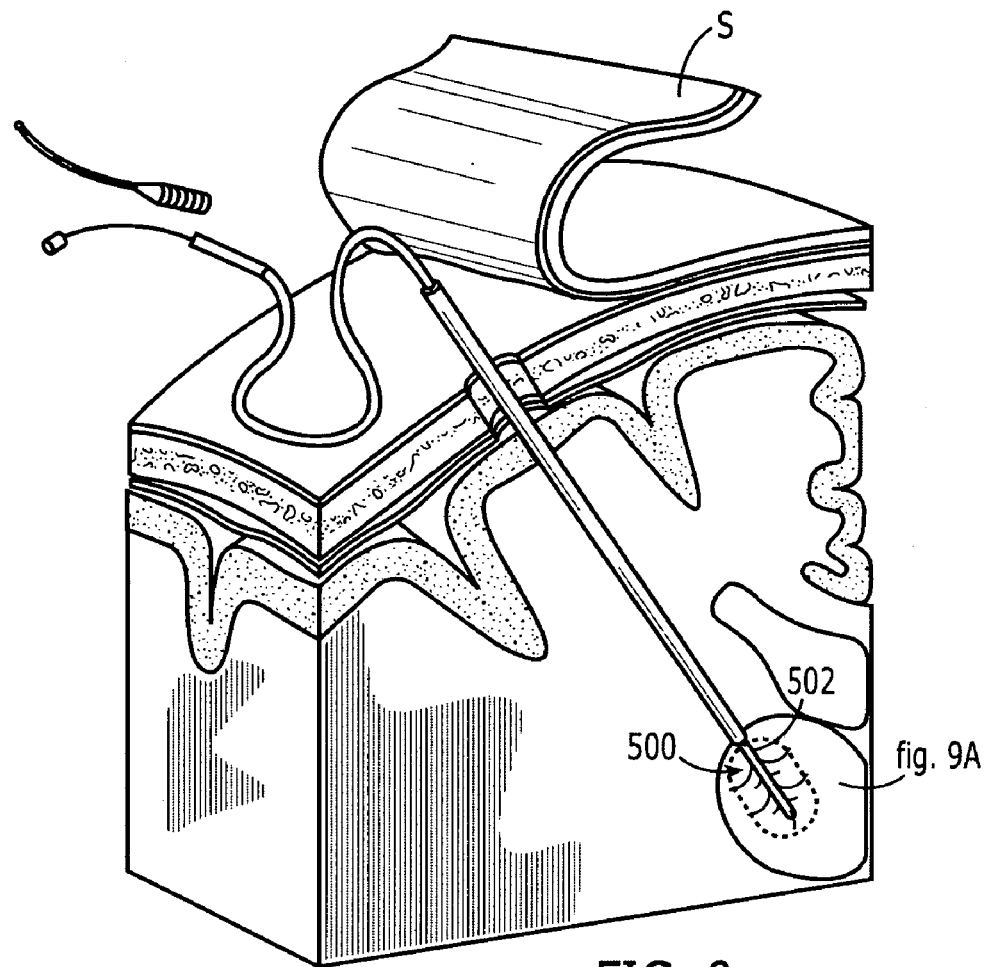
FIG. 9 shows an embodiment of an infusate delivering apparatus of the present invention implanted within a patient's brain.

It is well known that infused drugs or chemicals are more efficacious if delivered directly to desired locations of the human brain, rather than delivered indirectly through an intravenous drip and carried through the patient's blood stream. FIG. 9 shows infusate probe 500 positioned in a brain to deliver infusates to targeted portions of the patient's brain. It is within the scope of the present invention that infusate probe 500 could be used with the scalp S replaced. When scalp S is replaced, infusate could be withdrawn from a reservoir located either outside or inside the patient's body. When a patient uses an interior reservoir, infusate probe 500 could be used outside an operating room environment.

Figure 9A:
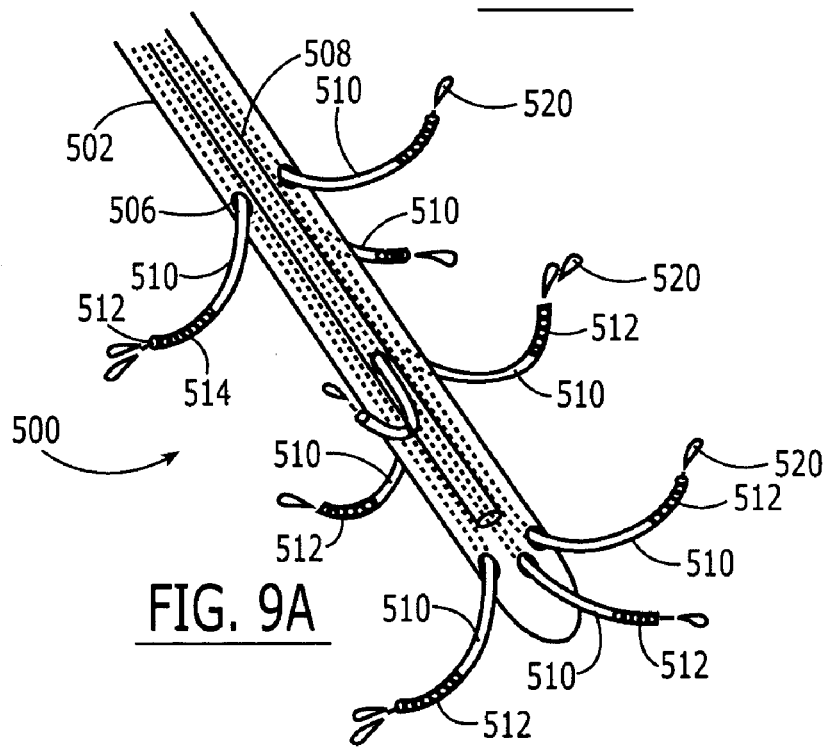
FIG. 9A is an alternative embodiment of an infusate delivering apparatus of the present invention.
Figure 9B:
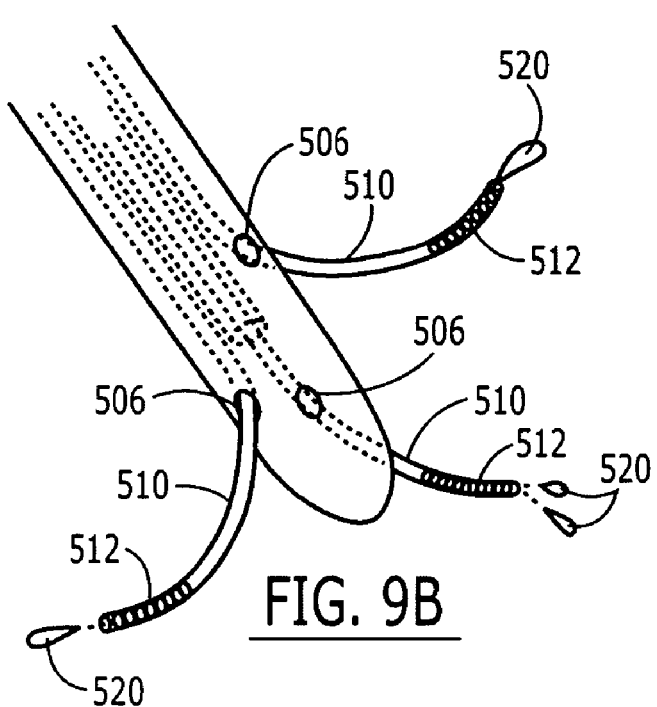
FIG. 9B is an alternative embodiment of the tendrils of the present invention using interior passages to deliver infusate along the tendrils of the infusate delivering apparatus of the present invention.

FIGS. 9 and 9A shows an infusate delivery probe 500. Infusate delivery probe 500 includes shaft 502, openings 506, stiffener 508, tendrils 510, radio frequency positioners 512 and lumens 518. Shaft 502 may employ stiffener 508. A surgeon may elect to use stiffener 508 if he desires a more rigid infusate delivery probe 500. A surgeon electing to use a less rigid probe 500, would use elect to remove stiffener 508. Tendrils 510 could be selectively urged outward through openings 506. It is desirable to obtain accurate information about the position of the terminal ends of tendrils 510, using RTF positioners 512 because infusate 520 can be more accurately delivered to a desired location in the human brain if the position of tendrils 510 is accurately known. Probe 500 is placed using standard techniques such as frame based, frameless or image guided placement techniques. In addition, RTF positioners 512 allow a surgeon to identify the precise location of each tendril 510. This allows a surgeon to selectively deploy a tendril 510 and deliver infusate to a targeted portion of the brain. In the embodiment of probe 500 seen in FIGS. 9 and 9A, it is preferable for infusate 520 to be delivered through the terminal ends of tendrils 510.

Figure 9C:
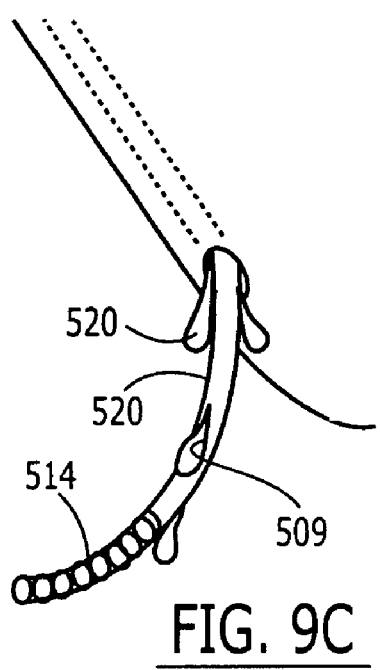
FIG. 9C is an alternative embodiment of the tendrils of the present invention using weep holes to deliver infusate along the tendrils of the infusate delivering apparatus of the present invention.

FIG. 9C shows an alternative embodiment of tendril 510 where infusate 520 is delivered through weepholes 509 located along tendril 510. This alternative embodiment may also use RTF positioners 512 to allow a surgeon to identify the precise location of each tendril 510.

Figure 9D:
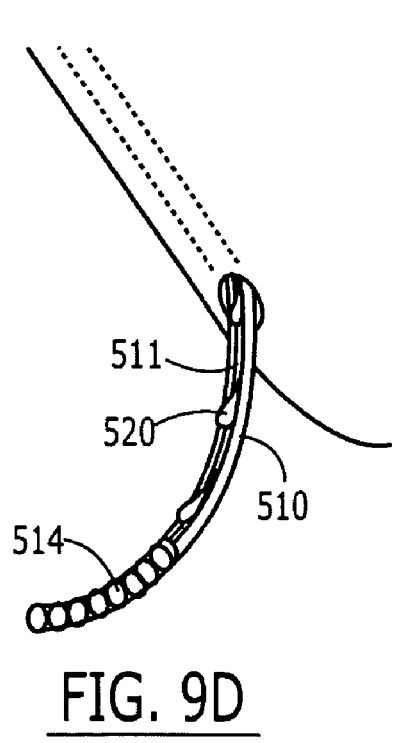
FIG. 9D is an alternative embodiment of the tendrils of the present invention using a gutter to deliver infusate along the tendrils of the infusate delivering apparatus of the present invention.

FIG. 9D shows an alternative embodiment of tendril 510 where infusate is delivered through a gutter 511 disposed longitudinally along tendril 510. This alternative embodiment may also use RTF positioners 512 to allow a surgeon to identify the precise location of each tendril 510.

Figure 10:
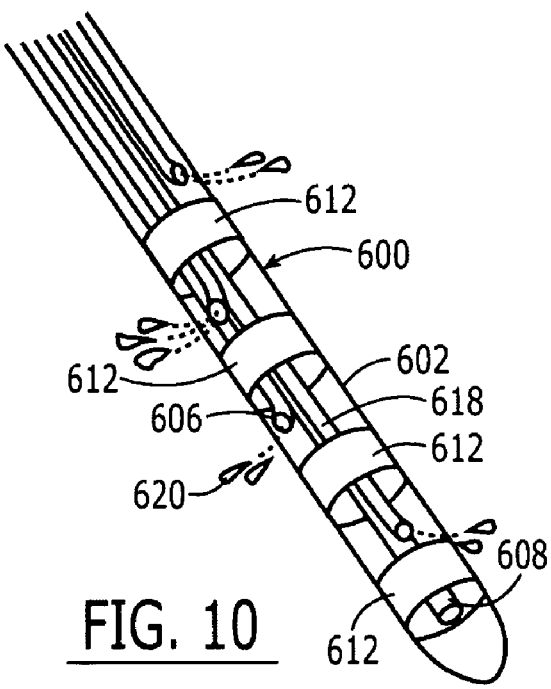
FIG. 10 is an alternative embodiment of an infusate delivering apparatus of the present invention.

FIG. 10 shows an alternative infusate delivery probe 600. Probe 600 includes shaft 602, openings 606, stiffener 608, electrodes 612 and lumens 618. Shaft 602 may employ stiffener 608. A surgeon may elect to use stiffener 608 if he desires a more rigid infusate delivery probe 600. A surgeon electing to use a less rigid probe 600, would use elect to remove stiffener 608. Infusate 620 flows out from a reservoir either external to the patient or surgically implanted within the patient and passes into the brain through lumens 618. Electrodes 612 allow electrical stimulation a patient's brain while also delivering infusate 620 as appropriate.

Figure 11:
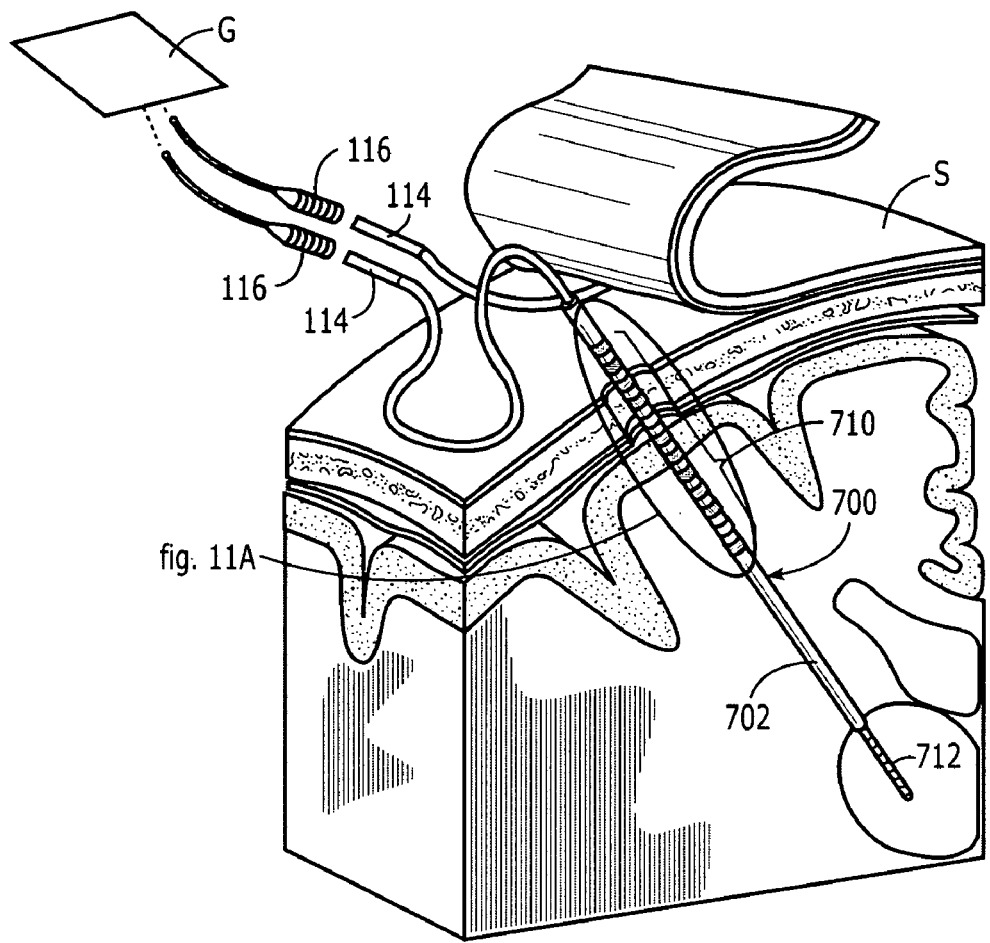
FIG. 11 is a perspective view of a depth graduated deep brain stimulation electrode of the present invention.
Figure 11A:
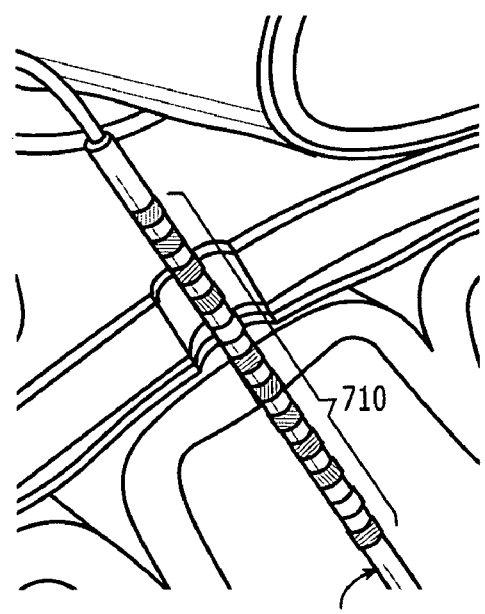
FIG. 11A is a detailed perspective view of the depth graduated deep brain stimulation electrode and left/right connector designators of the present invention.

FIG. 11 shows a depth graduated deep brain stimulation probe 700. Currently, deep brain stimulating probes P do not allow a surgeon to determine the depth that the probe P is inserted into the patient's brain. Indeed, as seen in FIG. 1, unless the surgeon has access to real time fluoroscopic imaging to monitor probe P's position, there are few if any means to allow a surgeon to precisely maintain the depth of probe P and precisely determine the position of electrodes A, B, C or D. If a surgeon knows the depth that he needs to insert probe P, or any alternative embodiment discussed in the present application, the surgeon could determine which color band 710 corresponded to the appropriate depth and insert probe 700 into the patient's brain only until the color band for this depth is just visible above the insertion point into the patient's brain.

Figure 11B:
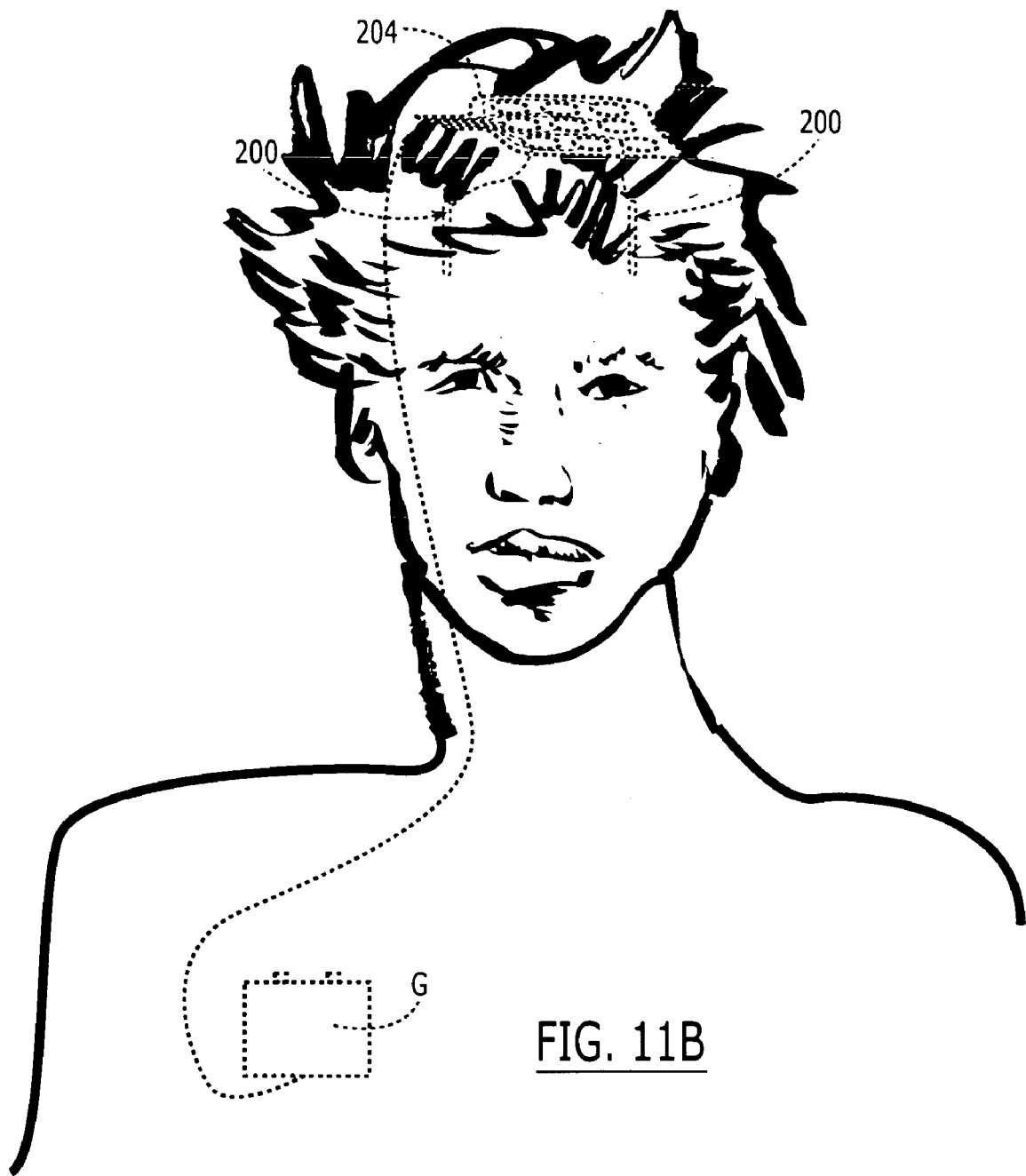
FIG. 11B is a perspective view of a surgically implanted neurostimulator, also known as a "pulse generator", with deep brain stimulation electrodes implanted in a patient's brain using the depth graduated deep brain stimulation electrode of the present invention.

FIGS. 11 and 11B shows that at the present time, lines 114 are not laterally distinguishable. In other words, a surgeon may be uncertain which line 114 is connected to the left and right connections of pulse generator G, seen in FIG. 11B, because lines 114 are implanted under the patient's skin. Therefore, it is desirable to label each line 114 as "left" or "right" along the entire length of the line 114. Alternatively, it may be desirable to chose alternative colors for left line 114 and right line 114. Conventionally, green is chosen for left and red for right. However, any system could work if different colors or markings were selected to distinguish lines 114. Additional information encoded onto the electrode might include the anatomic target site of the electrode or any other data that might be useful. The information on the electrodes could be depicted in any form of colors, symbols, letters, radio opaque markers that could be visualized by x-ray, or even small RF tags that could be interrogated by an RF reader device.

FIG. 12 shows subdural electrode shield 800. Subdural electrode shield includes case 802 and storage slot 804. In the embodiment seen in FIG. 12, lines 114 are coiled around case 802 and inside storage slot 804. When a surgeon is implanting probe P, the surgeon will be able to coil additional length of electrode inside storage slot 804. In this way, a surgeon can also more readily avoid confusion over left and right lines 114 and protect the electrode leads from inadvertent injury when being externalized later or kinked or damaged through rough handling while trying to jam the electrodes under the skin in a haphazard fashion as they attempt to spring out of the subcutaneous pocket. It should be noted that in its preferred embodiment, subdermal electrode shield 800 is implanted under a patient's scalp or any subcutaneous area. Other embodiments of this device could include the capacity to simply uncoil a small amount of the electrode so that it could be attached to the rest of the mechanism without having to uncoil the entire length of the electrode from the protective device.

FIG. 12A shows subdermal electrode shield 800'. Subdermal electrode shield includes casing 802', internal coiled spring 803' [not show], plug 805' and mouth 807'. Lines 114 pass through mouth 807' before connecting to probes P. Plug 805' electrically interconnect lines 114 to pulse generator G. Because subdural electrode shield 800' is spring loaded, excess line 114 is withdrawn inside casing 802' and excess line 114 is not exposed. A surgeon could "crimp" mouth 807' to prevent line 114 being withdrawn inside casing 802'. It should be noted that in its preferred embodiment, subdural spring loaded electrode shield 800's is implanted under a patient's scalp or any other desired subcutaneous area. Other embodiments of this device could include the capacity to simply uncoil a small amount of the electrode so that it could be attached to the rest of the mechanism without having to uncoil the entire length of the electrode from the protective device.

FIG. 12B shows subdermal electrode shield 800". Subdermal electrode shield 800" includes a casing 802" and a mouth 807". When a surgeon has completed implanting a probe P, the surgeon will be able to store any additional length of lines 114 inside shield 800". In this way, a surgeon can also more readily avoid confusion over left and right lines 114 and can protect the electrode leads from inadvertent injury when being externalized later or being kinked or damaged from rough handling while attempting to jam the electrodes under the skin in a haphazard fashion as they out of the subcutaneous pocket. It should be noted that in its preferred embodiment, subdermal electrode shield 800" is implanted under a patient's scalp or any subcutaneous area. Other embodiments of this device could include the capacity to simply uncoil a small amount of the electrode so that it could be attached to the rest of the mechanism without having to uncoil the entire length of the electrode from the protective device.

While the invention has been illustrated and described in detail in the drawings and description, the same is to be considered as an illustration and is not limited to the exact embodiments shown and described. All equivalents, changes and modifications that come within the spirit of the invention are also protected by the claims that are set forth below.

What is claimed is:

1. A deployable probe configured for stimulating deep brain tissue, comprising:
    a shaft having a proximal end, a distal end, and a hollow section;
    at least one opening on the distal end of said shaft, said opening configured for connecting the hollow section to adjacent brain tissue; and
    a plurality of extendable tendrils, each with a proximal end and a distal end, each said tendril configured to selectively move from a first position contained within the hollow section to a second position adjacent said brain tissue, said tendril configured to deliver treatment to the brain tissue; and
    a fluid-actuated deployer linked to said tendrils, said deployer configured to independently move each tendril with respect to the other tendrils from said first position to said second position.

2. The probe of claim 1, wherein the fluid-actuated deployer comprises a plurality of fluid lines, each line with a proximal end and a distal end, the distal end of each fluid line attached to one of said tendrils and the proximal end connected to an actuation reservoir.

3. The fluid-actuated deployer of claim 2 further comprising a percutaneous injector and a plurality of subcutaneous actuation reservoirs, wherein each of the subcutaneous actuation reservoirs is configured to independently deploy one of the tendrils.

4. The probe of claim 1 wherein the treatment includes any of the group consisting of one or more of the following: delivery of a pharmaceutical or delivery of a bioactive agent.

5. The probe of claim 4 wherein said shaft is arcuate at the distal end.

6. The probe of claim 4 further comprising a radio-opaque marker attached to the distal end of said tendrils.

7. The probe of claim 4 wherein the shaft further comprises a graduated depth indicator for determining the depth of probe insertion and the graduated depth indicator is fixedly attached to the shaft.

8. A deployable probe configured for stimulating deep brain tissue, comprising:
    a shaft having a proximal end, a distal end, and a hollow section;
    at least one opening on the distal end of said shaft, said opening configured for connecting the hollow section to adjacent brain tissue; and
    a plurality of extendable tendrils, each with a proximal end and a distal end, each said tendril configured to selectively move from a first position contained within the hollow section to a second position adjacent said brain tissue, said tendril configured to deliver treatment to the brain tissue; and
    a fluid-actuated deployer linked to said tendrils, said deployer configured to independently move each tendril with respect to the other tendrils from said first position to said second position, wherein the fluid-actuated deployer further comprises a plurality of fluid lines, each line with a proximal end and a distal end, the distal end of each fluid line attached to one of said tendrils and the proximal end connected to an actuation reservoir.

9. The fluid-actuated deployer of claim 8 further comprising a percutaneous injector and a plurality of subcutaneous actuation reservoirs, wherein each of the subcutaneous actuation reservoirs is configured to independently deploy one of the tendrils.

10. The probe of claim 8 wherein the treatment includes any of the group consisting of one or more of the following: delivery of a pharmaceutical or delivery of a bioactive agent.

11. The probe of claim 10 further comprising a radio-opaque marker attached to the distal end of said tendrils.

12. The probe of claim 10 wherein the shaft further comprises a graduated depth indicator for determining the depth of probe insertion and the graduated depth indicator is fixedly attached to the shaft.

13. The probe of claim 8 wherein the treatment is electrical stimulation.

14. The probe of claim 13 further comprising a radio-opaque marker attached to the distal end of said tendrils.

15. The probe of claim 13 wherein the shaft further comprises a graduated depth indicator for determining the depth of probe insertion and the graduated depth indicator is fixedly attached to the shaft.

* * * * *